United States Patent [19]

Kalsta et al.

[11] Patent Number: 5,104,662

[45] Date of Patent: Apr. 14, 1992

[54] METHOD OF ENCAPSULATING BIOLOGICALLY ACTIVE SUBSTANCES WITH MUCIN, A CAPSULE PRODUCED BY THE METHOD, AND A FODDER CONTAINING SUCH CAPSULES

[75] Inventors: Hannu Kalsta; Eeva-Liisa Syväoja, both of Espoo; Juha Nousiainen; Jouko Setälä, both of Helsinki, all of Finland

[73] Assignee: Valio Meijerien Keskusosuusliike, Helsinki, Finland

[21] Appl. No.: 598,222

[22] Filed: Oct. 16, 1990

[30] Foreign Application Priority Data

Nov. 2, 1989 [FI] Finland .................................. 895216

[51] Int. Cl.$^5$ ....................... A61K 9/48; A61K 47/42; A61K 35/74; A23K 1/16
[52] U.S. Cl. ..................... 424/451; 424/438; 424/442; 424/93 C; 424/551; 424/488
[58] Field of Search ................ 424/451, 438, 442, 93, 424/551

[56] References Cited

U.S. PATENT DOCUMENTS

| | | | |
|---|---|---|---|
| 4,424,216 | 1/1984 | Cerami et al. | 424/601 |
| 4,438,100 | 3/1984 | Balslev et al. | 424/609 |
| 4,822,534 | 4/1989 | Lencki et al. | 424/455 |
| 4,842,863 | 6/1989 | Nishimura et al. | 424/498 |
| 4,963,367 | 10/1990 | Ecanow | 424/460 |

*Primary Examiner*—Thurman K. Page
*Assistant Examiner*—E. J. Webman
*Attorney, Agent, or Firm*—Finnegan, Henderson, Farabow, Garrett & Dunner

[57] ABSTRACT

The invention relates to a method of encapsulating biologically active substances by gelling them with intestinal mucus (mucin). The invention is also concerned with a capsule produced by the method, its use as a fodder admixture, and a fodder containing such capsules.

17 Claims, No Drawings

METHOD OF ENCAPSULATING BIOLOGICALLY ACTIVE SUBSTANCES WITH MUCIN, A CAPSULE PRODUCED BY THE METHOD, AND A FODDER CONTAINING SUCH CAPSULES

The invention relates to a method of encapsulating biologically active substances by gelling them with intestinal mucus, a capsule produced by the method, its use as a fodder admixture, and a fodder containing such capsules.

A frequent problem with giving biological substances orally is that the substances are degraded in the digestive tract, usually in the stomach, before reaching the intestine, where they are supposed to act. To solve this problem, active substances have been encapsulated by a protective material withstanding the conditions prevailing in the stomach so that they will not degrade before the intestines.

The encapsulation method has been employed with different drugs. In his extensive survey, Sanders (1985, Chem. & Eng. News, April 1: 31) states that drugs are encapsulated to obtain controlled release of the drug. Encapsulation uses various hydrogels (such as hydroxy ethyl methacrylate), polymer matrices (such as ethylene vinyl acetate) or bioadhesive matrices (such as carboxymethyl cellulose), that is, the employed encapsulation methods have been synthetic.

Finnish Patent Specification 64173 discloses a method of encapsulating fodders, nutrients, pharmaceutical preparations, etc. The encapsulating material consists of a mixture of polymers in which one main component is methyl acrylate. Japanese Published Specification 84/113192 also discloses a method of encapsulating physiologically active materials. The encapsulating material consists of $CaCO_3$, HCl and wax.

It has now been unexpectedly found that intestinal mucus is extremely suitable for the encapsulation of biologically active substances. A new encapsulation method has thus been developed which is based on the utilization of the functional, biochemical and physiological properties of glycoproteins contained in the intestinal mucus. The method is technically simple and the encapsulation material does not have any disadvantageous side effects as it is not synthetic but a natural product.

In particular, the production of the protective capsule utilizes the reversible water binding ability of intestinal mucus, which enables the swelling of a capsule of freeze-dried intestinal mucus in the digestive juices; the enzymatic degradation resistance of the mucus in the stomach; and its good degradability in the small intestine, which together enable the conveyance of the biologically active substances through the stomach into the small intestine without that the substances lose their ability of functioning, and the release of the functionable, biologically active substances in the distal end of the small intestine. Having been conveyed into the digestive tract with the capsule material, biological factors present in the mucus, such as lysozyme, pancreatic enzymes and other digestive enzymes contained in the intestinal juice, have a favourable effect on the digestion.

CONSTITUTENTS OF THE INTESTINAL MUCUS AND THEIR PROPERTIES

The properties of intestinal mucus are discussed in, e.g., *Journal of Applied Bact.* 66 (1989): 407–417, *Physiology of Gastrointestinal Tract*, 2nd, ed., Raven Press, London.

The epithelium of the digestive tract is covered with intestinal mucus or mucin. Its function is to protect the epithelium and to act as a lubrication agent. The intestinal mucus consists of water, blood serum and cellular macromolecules e.g., glycoproteins, and, somatic and microbial cells and glycoproteins.

The structure of mucin-glycoproteins typically contains peptide subunits and oligosaccharide chains bonded to them. Each subunit consists of a single long peptide the molecular weight of which is several hundreds of thousands of daltons. When the peptides are joined end to end, a glycoprotein is obtained the molecular weight of which is several millions of daltons.

The oligosaccharide chains usually contain 2 to 8 sugar molecules. Typical sugars include N-acetyl galactose amine (GalNAc) and N-acetyl neuraminic acid (NeuAc) i.e., sialic acid.

The oligosaccharide chains are so linked together that the peptide subunit contains several both densely glycosylated and non-glycosylated so-called naked points.

The composition and structure of oligosaccharide chains as well as their local density in the peptide chain affect greatly the solubility, viscosity, electric charge and denaturation of glycoproteins. Generally speaking, the oligosaccharide chains improve the chelating ability of calcium, water binding properties, gel formation ability and proteolysis resistance in mucin-glycoproteins.

Due to the influence of the oligosaccharide chains bonded to the mucin-glycoproteins, the mucinglycoproteins are elastic and partially spiral macromolecules strongly hydrated in an aqueous solution, and appear as ribbon-like stretches (4 to 6 $\mu$m) in electron microscope pictures.

FORMATION OF INTESTINAL MUCUS IN THE SMALL INTESTINE

Mucin-glycoproteins are synthesized in the mucous cells of the epithelium of the small intestine and condensed into the grains present in them. The condensation is made more effective by bivalent cations ($Ca^{2+}$, $Mg^{2+}$ and $Zn^{2+}$). Especially calcium ions are bonded strongly to the oligosaccharide chains and contribute to the condensation of the glycoproteins and help them to remain condensed.

The mucous cells are differentiated into goblet cells which secrete glycoprotein-containing grains into the small intestine. Cations are diffused out of the grains and intestinal juice is absorbed into the grains. The glycoproteins thereby bind water as a result of which the grains swell drastically. The hydration of the glycoproteins results in the formation of gel-like mucus, mucin, in the intestine.

As a gel, the intestinal mucus deviates from agar and alginate gels which are more elastic and chemically more uniform than intestinal mucus. This is due to the regular intermolecular bonds. Intestinal mucus is more porous than the above-mentioned mucus gels of plant origin, which enables free diffusion of nutrients and epithelial secretions in the intestine.

The amount of mucin-glycoprotein required for the formation of intestinal mucus varies from 15 to 50 mg/ml. Within this concentration range the intestinal mucus is a soft glycoprotein-based gel the inner cavities of which are filled with intestinal juice containing, e.g., water, lipids, enzymes, detached epithelial cells, and micro-organisms.

DEGRADATION OF INTESTINAL MUCUS IN THE DIGESTIVE TRACT

Intestinal mucus is degraded by pepsin in the stomach, and proximally in the small intestine by the proteases of the pancreas and the mucosa, and distally in the small intestine by glycosidases and microbial proteases. The degradation implies reduction in the thickness of the mucus layer.

In the stomach the intestinal mucus is first diluted in the gastric juice so that it swells. When pepsin degrades glycoproteins, the naked points of the subunits release soluble glycopeptides which are not again able to form gel.

In the small intestine, the peptide chains of the glycoprotein subunits will not be cleaved until the glycosidases have eliminated a majority of the oligosaccharide chains the high electric charge of which prevents the action of the proteases. In the distal end of the small intestine, a rapid reduction occurs in the viscosity of intestinal mucus as the glycoproteins are degraded into soluble glycopeptides which are not again able to form gel.

In the large intestine, the glycoproteins and the peptide subunits are degraded by the action of proteases, proteinases, glycosidases and sulphatases. The mucin-glycoprotein content of faeces is normally very low.

DIFFERENCES BETWEEN THE INTESTINAL MUCUS OF DIFFERENT ANIMALS

The amino acid profile of mucin-glycoproteins present in the intestinal mucus of different mammalian species is rather uniform as well as the number and kind of carbohydrates, whereas the length of the carbohydrate or oligosaccharide chains may vary considerably.

The protection and lubrication properties of intestinal mucus are, however, very similar in different animal species.

Properties common to all mucin-glycoproteins include large size, high content of carbohydrates and water binding properties, which together constitute the basis of the properties and use of the mucin capsule of the present invention.

The encapsulation method of the invention is characterized in that biologically active substances are gelled with an effective amount of intestinal mucus. To enable easy rationing, it is preferable to perform the gelling in the presence of alginate and calcium ions. Calcium ions cause the precipitation of alginate. Any biologically active substances can be encapsulated, such as micro-organisms, enzymes, drugs, antibodies and antibiotics. The method is particularly suitable for the encapsulation of micro-organisms or their biologically active components. Preferably, the micro-organisms are lactic acid bacteria and the biologically active components are enzymes. Lactic acid bacteria, such as the bacteria of the *Lactobacillus* and *Streptococcus* genera, are used as intestinal probiotics because of their favourable effect on the intestinal activities. They, for instance, reduce the pH, so that the growth of disadvantageous intestinal bacteria is prevented. A mixture of adhesive and non-adhesive lactic acid bacteria is often used as a probiotic.

The present invention is also concerned with a capsule which is characterized in that it comprises intestinal mucus and biologically active substances gelled with the mucus. The active substances are preferably micro-organisms, particularly advantageously lactic acid bacteria. The invention further concerns methods for using a capsule of intestinal mucus containing biologically active substances, such as micro-organisms, preferably lactic acid bacteria, as a fodder admixture, and a fodder comprising a capsule of intestinal mucus containing biologically active substances, such as micro-organisms, preferably lactic acid bacteria. Encapsulated biologically active substances can also be used as pharmaceuticals.

EXAMPLE 1

Wet mucin was taken from the small intestine of a pig mechanically by squeezing when incising the intestine. The mechanical squeezing was followed by rinsing and wash with water at 40° C. Wet mucin was dried by lyophilization and then refined in a mortar.

4 g of lyophilized lactic acid bacterial preparation and 6 g of lyophilized mucin powder were mixed with 50 to 150 ml of 1% sodium alginate solution to obtain an even mass. The mixture was allowed to drop from lyer-base syringes from the height of 1 m into a 1 M $CaCl_2$ solution at $+4$ to 40° C. The resultant capsules were kept in this solution and at this temperature for no more than 30 minutes, whereafter they were rinsed twice with cold water and lyophilized dry.

The quantity of lactic acid bacteria of the dry capsules so obtained was determined anaerobically by a plate count method using MRS agar (37° C., 3 days), on the basis of which rations for the pig trials were calculated. The total count of lactic acid bacteria was $10^7$ cfu/g, which corresponded to the amount added at the preparation stage.

EXAMPLE 2

In vitro digestibility trials were carried out with the capsules prepared in Example 1. 2.5 g of capsules was first melted in a water bath at 37° C in 100 ml of 0.1 N hydrochloric acid, to which 10 mg of pepsin had been added. After incubation for four hours, the pH of the filtrate was adjusted to 8.0 by sodium hydroxide and 50 ml of 0.067 M phosphate buffer containing 27 mg of pancreatin was added. Incubation was continued for 24 hours at 37° C. The pepsin treatment had no effect on the capsules. The pancreatin digestion also did not break the capsules but they had already swollen to a very great extent.

EXAMPLE 3

The trial was carried out as a physiological test with four pigs each about 30 kg and equipped with a cannula in the ileum of the small intestine for sampling. The pigs were fed twice a day with a barley-soybean diet which met the nutrient requirements of the pigs. The trial was designed as a group period trial, in which the length of one period was two weeks. During the first period, two pigs were given unencapsulated lactic acid bacteria (LAB) and two pigs were given LAB encapsulated in intestinal mucus. During the second period, the treatment was reversed. The lactic acid bacterium used was freeze-dried *Lactobacillus fermentum*, isolated from the contents of the small intestine of a pig.

The lactic acid bacteria were given to the animals in the same concentration level, which was 2 g/pig/day. During the four last days of each period, the faeces and the contents of the small intestine were sampled (TABLE).

The encapsulated LAB preparation gave a significantly ($P<0.05$) higher production of volatile fatty acids and a higher production of lactic acid in the ileum. The higher production of acids had a favourable effect on the pH value of the contents of the ileum, which was nearly significantly ($P<0.06$) lower with pigs which were given the encapsulated LAB preparation. The LAB preparations given in powdered or encapsulated form had similar effect on the quantity of lactic acid bacteria in the contents of the ileum, which indicates that the encapsulated *L. fermentum* bacteria as well as their enzymes were more functionable (higher acid production) This proves the favourable effect of encapsulation.

No capsules were found in the sampled faeces of the animals, which shows that the capsule degrades completely in the digestive tract of the pig.

TABLE

Effect of LAB preparations on the chemical and microbiological composition of the contents of the small intestine of pigs

|  | *L. fermentum*, powder | *L. fermentum*, encapsulated | SEM | P value |
|---|---|---|---|---|
| Lactic acid, mmol/l | 56.8 | 57.2 | 22.8 | 0.96 |
| Volatile fatty acids, mmol/l | 9.0 | 11.2 | 1.8 | 0.05 |
| Acetic acid, mol % | 12.8 | 13.3 | 2.0 | 0.67 |
| Propionic acid, mol % | 1.8 | 3.1 | 1.6 | 0.12 |
| Butyric acid, mol % | 0.4 | 0.8 | 0.5 | 0.15 |
| Lactic acid, mol % | 85.0 | 82.4 | 3.1 | 0.68 |
| pH | 6.93 | 6.80 | 0.2 | 0.06 |
| Lactic acid bacteria, cfu/g | $1.2 \times 10^8$ | $1.1 \times 10^8$ | $6.7 \times 10^2$ | 0.92 |

SEM = standard error of mean

We claim:

1. A method for encapsulating biologically active substances, comprising adding intestinal mucus in an amount effective for gelling the biologically active substances.

2. A method according to claim 1, wherein the gelling is carried out in the presence of alginate and calcium ions.

3. A method of claim 1, wherein the biologically active substances are micro-organisms or biologically active components thereof.

4. A method according to claim 3, wherein the micro-organisms are lactic acid bacteria.

5. A method according to claim 1, wherein the biologically active substances are enzymes.

6. A capsule comprising intestinal mucus and biologically active substances gelled with said mucus.

7. A capsule according to claim 6, wherein the biologically active substances are micro-organisms.

8. A capsule according to claim 7, wherein the micro-organisms are lactic acid bacteria.

9. A method which comprises using a capsule of intestinal mucus containing biologically active substances in a fodder admixture.

10. A method according to claim 9, wherein the biologically active substances are micro-organisms.

11. Fodder comprising a capsule of intestinal mucus containing biologically active substances.

12. Fodder according to claim 11, wherein the biologically active substances are micro-organisms.

13. Fodder according to claim 12 wherein the micro-organisms are lactic acid bacteria.

14. A method according to claim 10 wherein the micro-organisms are lactic acid bacteria.

15. A method according to claim 1, wherein the biologically active substances are antibiotics.

16. A method according to claim 1 wherein the biologically active substances are antibodies.

17. A method according to claim 1 wherein the biologically active substances are enzymes.

* * * * *